US007871969B2

(12) United States Patent
Myers

(10) Patent No.: US 7,871,969 B2
(45) Date of Patent: Jan. 18, 2011

(54) MILD CLEANSING SOAP BARS

(75) Inventor: E. Gary Myers, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 780 days.

(21) Appl. No.: 11/284,542

(22) Filed: Nov. 22, 2005

(65) Prior Publication Data

US 2007/0117728 A1 May 24, 2007

(51) Int. Cl.
*A61K 7/50* (2006.01)

(52) U.S. Cl. ....................... 510/141; 510/152; 510/139; 510/153; 510/155

(58) Field of Classification Search ....................... None
See application file for complete search history.

(56) References Cited

U.S. PATENT DOCUMENTS

| | | | | |
|---|---|---|---|---|
| 4,557,853 | A | 12/1985 | Collins | |
| 5,910,476 | A * | 6/1999 | Kinsman et al. | 510/447 |
| 6,440,908 | B2 * | 8/2002 | Racherla | 510/122 |
| 6,764,991 | B2 * | 7/2004 | Puvvada et al. | 510/458 |
| 6,818,603 | B2 | 11/2004 | Aleles et al. | |
| 2001/0046949 | A1 * | 11/2001 | Agrawal et al. | 510/141 |
| 2005/0123574 | A1 | 6/2005 | Abbas et al. | |
| 2005/0187129 | A1 * | 8/2005 | Chakrabarty et al. | 510/392 |
| 2005/0192189 | A1 | 9/2005 | Wagner et al. | |

* cited by examiner

*Primary Examiner*—Necholus Ogden, Jr.
(74) *Attorney, Agent, or Firm*—Frank T. Barber

(57) ABSTRACT

A personal cleansing composition in solid or bar form which is mild to the skin and very effective in removing dirt and grime from the body, particularly the hands. Importantly, such soap bars do not have a noticeable abrasive feel when in contact with the skin. Another feature is that the bar exhibits a so called “drag effect” when the soap bar is used for washing.

1 Claim, No Drawings

MILD CLEANSING SOAP BARS

FIELD OF THE INVENTION

The present invention relates generally to personal cleansing soap bars which are mild to the skin but which are superior to customary toilet soap bars in removing dirt and grime from the skin but without a noticeable abrasive feel to the bar.

BACKGROUND OF THE INVENTION

Personal care compositions such as toilet soaps are of course well known. Such toilet soaps in bar form are usually formulated with a wide variety of additives to provide user benefits that are not necessarily inherent in the soap itself. For example, additives are employed to enhance lathering of the soap, to ensure mildness, and to enhance its antibacterial qualities. Many years ago a soap bar containing pumice was brought to market to be used for heavy duty personal cleansing such as to remove heavy soils such as oil, grease and clay. The product is still commercially available and contains about 20% by weight of pumice which is used to mechanically assist removal of such soils. Although effective, such a soap with pumice can damage sensitive skin. It is known in the soap industry that these higher levels of pumice can affect soap making equipment, particularly plodder screws.

So called exfoliating soap bars are also known but many are considered irritating to the skin due to the fact that they have high levels of certain harsh or marginally effective exfoliants. Examples of such prior art toilet bars with exfoliant particles or beads are polytyrene beads, silica, walnut shells, apricot seed and the like as described in U.S. Pat. Nos. 6,376,441; 6,342,470; 6,384,000 and 6,074,998. The particles are usually very hard and impart an undesirable abrasive feel to the bars and can be noticed by the user when bathing or washing the hands.

SUMMARY OF THE INVENTION

The present invention is directed to a personal cleansing composition in solid or bar form which is mild to the skin and very effective in removing dirt and grime from the body, particularly the hands. Importantly, such soap bars do not have a noticeable abrasive feel when in contact with the skin. Another important feature is that the composition of the bar is such that it exhibits a so called "drag effect" when the soap bar is used for washing. For example, when the soap bar of this invention is used to wash the hands, the user normally rotates the bar in his/her hands and it is this rotation of the bar which is slowed due to the composition of the bar. This drag effect seems to enhance the removal of dirt and grime.

DETAILED DESCRIPTION OF THE INVENTION

In a preferred embodiment, the composition of this invention includes:

a. from about 55% to about 65% by weight of a water-soluble soap which for purposes of describing this component of the invention has the meaning as normally understood in the soap art or in its popular sense, i.e., the alkali metal or alkanol ammonium salt of alkane or alkene monocarboxglic acids. The counterion of such salts includes sodium, potassium, ammonium and alkanol ammonium ions as well as other ions known in the art. Sodium is preferred. Typically the soap component comprises salts of long chain fatty acids having chain lengths of the alkyl group of such fatty acids from about 8 carbon atoms to about 18 carbon atoms in length. The particular length of the alkyl chain is selected for various reasons, including cleaning quality, lathering, cost and the like. A preferred soap is the sodium salt of an 85/15 ratio of tallow to coco fatty acids. The soap can also contain sodium palmatate or palm kernalate. It is preferred that the soap contain from about 8% to about 12% by weight of moisture, preferably about 8.5%.

b. from about 12% to about 35% by weight of a water insoluble particle which serves to enhance the removal of dirt and grime but which does not give a noticeable abrasive feel when incorporated into the bar composition and when the bar is used to bathe the skin. It has been found that such particles should have a hardness ranging from about 2 to about 3 on the Moh's Hardness Scale preferably about 3. The Moh's scale is a scale for determining the relative hardness of a mineral. The affect of hardness which is measured by the Moh's test is the scratchability of a mineral. Thus this scale is useful in identifying the type of particles useful in the composition. It has further been found that limestone is very effective as a particle in the bar composition. Limestone is a combination of calcium carbonate (about 96.5%) and magnesium carbonate (about 3.1%). Another mineral which works well as a particle in the composition is dolomite which is similar to limestone in composition but is richer in magnesium and carbonate (CaMg) $CO_3$. Following is the size of the particles useful in the composition:

| U.S. Standard Mesh | % Passing |
|---|---|
| 60 | 100 |
| 100 | 98 |
| 200 | 81 |

As previously noted, the presence of the appropriate water insoluble particles crates a drag effect when the bar composition is used in bathing. As the user rotates the bar in the hands when bathing, this drag effect adds to the time that the bar is in contact with the skin and this is a factor in the bar being more effective at removing dirt and grime.

c. from about 1% to about 5% by weight of a synthetic surfactant which serves to help break down oils or grease that may be present on the skin. Such synthetic surfactant also serves to increase the flash foam of the composition giving better lather. More than 5% of the synthetic surfactant may effect the processing of the soap by adversely effecting the transport of the soap through equipment used in processing. A combination of a synthetic anionic surfactant (such as sodium lauryl sulfate) and a synthetic nonionic surfactant (sodium laureth sulfate) work well.

d. From about 0.10% to about 5% by weight of borax (sodium borate). The presence of the borax serves to boost the performance of the soap, soften water and help to emulsify any waxes or oils.

e. The following are optional ingredients:

Titanium dioxide: serves as optical brightener

Fragrance

Propylene glycol: serves as a carrier for the fragrance and as a skin conditioner Aloe Vera: skin conditioner

EXAMPLE 1

A personal cleansing bar was prepared having the following ingredients in percentages by weight. This example is provided for illustrative purposes and should not be considered as limiting the scope of this invention.

| Ingredient | % By Weight |
|---|---|
| Soap, sodium salt of tallow and coco fatty acids of an 85/15 ratio | 58% |
| Water | 9% |
| Limestone | 29% |
| $C_aCO_3$ | 96.5% |
| $M_gCO_3$ | 3.1% |
| Mohs Hardness | 3.0 |
| Physical analysis | |
| U.S. Standard Mesh | % Passing |
| 60 | 100 |
| 100 | 98 |
| 200 | 81 |
| Borax (sodium borate | 0.10% |
| Synthetic surfactant (Sodium lauryl sulfate) (Sodium laureth sulfate) | 2% |
| Optional ingredient Including $T_iO_2$, fragrance skin conditioners and glycerin in soap base | 2% |

Manufacture of Bar Compositions

The soap bar compositions of this invention can be manufactured using conventional soap making and processing equipment. The virgin soap pellets, dry additives, color slurry and perfume initially undergo a mixing process in an amalgamator mixer in order to surface coat the pellets with the components. The formulated pellets are then sent through a 5-roll mill to further homogenize the additives throughout the individual pellets. The mill creates ribbons of soap after which they are sent by belted conveyor to the first stage simplex plodder. This first stage plodder re-pelletizes the soap and delivers them directly into the hopper of the second (and final) stage simplex plodder. At this second stage the soap is extruded into a continuous, uniform slug. The continuous slug is cut into individual soap slugs by a bar cutter. The slugs continue onto the infeed belt of a double stroke Simplex press, where they are pressed into the final soap bar.

Comparison to Prior Art Soap Bar

A study was undertaken to determine the amount of soap lost when using the bar soap product of this invention as compared to a commercially available prior art soap product containing about 21% by weight of pumice and sold under the Lava® trademark. A principal object of the study was to calculate the amount of soap lost in washing hands with each product.

Thirty respondents were assembled for the handwashing test. They were instructed to wash their hands 3 times a day for 7 days and to wear gloves during all washes to eliminate any skin irritation. The following protocol was followed:

Protocol:

1. Rinse bar under water for 5 seconds.
2. Hold bar in RIGHT hand and rub bar over LEFT hand 10 strokes on palm, 5 strokes on back of hand. (1 stroke=rubbing bar up and down full length of hand)
3. Place bar in LEFT hand and repeat step 2 to wash RIGHT hand.
4. Rinse bar and put in dish, and rinse off hands.

The results of the study were as follows:

| | |
|---|---|
| Bar of this invention | |
| Average starting weight | 115.20 g |
| Average finish weight | 86.35 g |
| Grams lost per bar | 28.85 |
| Grams lost per wash | 1.37 |
| Washes per bar | 89 |
| Prior art bar | |
| Average starting weight | 116.56 g |
| Average finish weight | 75.88 |
| Grams lost per bar | 40.67 |
| Grams lost per wash | 1.94 |
| Washes per bar | 63 |

This study indicates that the bar soap of this invention lasted about 30% longer than the prior art pumice containing soap bar.

The invention claimed is:

1. A personal care cleansing bar composition having enhanced ability to remove dirt and grime from the skin, particularly the hands, said cleansing bar comprising about 58% by weight of a water soluble soap as the principal surfactant, about 9% by weight of water, about 2% by weight of synthetic surfactant, about 0.10% by weight by weight of borax and about 29% by weight of a water insoluble particle selected from the group consisting of limestone, dolomite or mixtures thereof having a hardness ranging from about 2 to about 3 on the Mohs Hardness Scale, said particles being dispersed throughout said bar composition and being of a size such that about 100% will pass through a 60 U.S. standard mesh sieve, about 98% will pass through a 100 U.S. standard mesh sieve, and about 81% will pass through a 200 U.S. standard mesh sieve, the presence of said particles in said bar composition creating a drag effect when the composition is used in bathing the skin which drag effect aids in removing dirt and grime from the skin.

* * * * *